United States Patent [19]

Iwamoto et al.

[11] Patent Number: 4,755,620

[45] Date of Patent: Jul. 5, 1988

[54] ACRYLATE COMPOUND AND COMPOSITION CONTAINING THE SAME

[75] Inventors: Osamu Iwamoto, Yokohama; Shinichiro Kunimoto, Fujisawa; Koshi Kusumoto, Kamakura; Toru Ono, Fujisawa, all of Japan

[73] Assignee: Tokuyama Soda Kabushiki Kaisha, Yamaguchi, Japan

[21] Appl. No.: 877,739

[22] Filed: Jun. 24, 1986

[30] Foreign Application Priority Data

Jun. 24, 1985 [JP] Japan .................................. 60-135873
Aug. 16, 1985 [JP] Japan .................................. 60-179320

[51] Int. Cl.$^4$ .................................................. C07C 69/52
[52] U.S. Cl. .................................. 560/224; 526/318; 523/116
[58] Field of Search .................................. 560/224

[56] References Cited

FOREIGN PATENT DOCUMENTS 85337  5/1982  Japan .................................. 560/205
255936  6/1972  U.S.S.R. .................................. 560/205

*Primary Examiner*—Paul J. Killos
*Attorney, Agent, or Firm*—Sherman and Shalloway

[57] ABSTRACT

Disclosed is an acrylate compound represented by the following general formula:

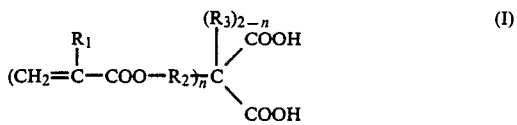

wherein $R_1$ stands for a hydrogen atom or an alkyl group having 1 to 4 carbon atoms, $R_2$ stands for an alkylene group having 2 to 20 carbon atoms, $R_3$ stands for a hydrogen atom or an alkyl group having 1 to 20 carbon atoms when n is 1, and n is 1 or 2.

A composition comprising this acrylate compound as one component has an excellent adhesiveness.

9 Claims, 4 Drawing Sheets

# 4,755,620

ACRYLATE COMPOUND AND COMPOSITION CONTAINING THE SAME

BACKGROUND OF THE INVENTION (1) Field of the Invention

The present invention relates to a novel compound and a composition comprising this acrylate compound as one component and having a good adhesiveness.

(2) Description of the Invention

Recently, adhesive are widely used in the fields of metals, organic polymers, ceramics, medical treatments and the like, and they play important roles for reducing the weight of apparatus, attaining an energy-saving effect and exerting a high performance. As the known reaction type adhesive, there can be mentioned an epoxy resin, a urethane resin, an unsaturated polyester and a cyanoacrylate adhesive. Of these reaction type adhesives, an adhesive having a high bonding strength is insufficient in that the curing speed is slow and aging should be carried out at a high temperature or for a long time, and an adhesive which is cured in a short time, such as a cyanoacrylate adhesive, is insufficient in that the water resistance is poor.

In contrast, an adhesive of the acrylate monomer type can be cured by various means such as heating, room temperature and light, and the curing time can be controlled within a broad range. However, the adhesive force of this adhesive is a so-called fitting force manifested on convexities and concavities of a surface to be bonded, which are formed by various surface treatments. Accordingly, development of an adhesive capable of exerting an adhesive force without any surface treatment is eagerly desired.

As means for satisfying this desire, there has been proposed a method in which a variety of carboxyl group-containing acrylate compounds are used for enhancing the adhesive force. For example, in Journal of The Japan Society for Dental Apparatus and Materials, 8, 14, pages 36–43, it is taught that acrylate compounds represented by the following formulae:

$$H_2C=\overset{\underset{\displaystyle CH_3}{|}}{C}-CO-NH-\underset{\underset{\displaystyle CH_2-COOH}{|}}{CH}-COOH$$

and $$CH_2=\overset{\underset{\displaystyle CH_3}{|}}{\underset{\underset{\displaystyle CONH-}{|}}{C}}-\bigcirc-N\overset{\diagup CH_2-COOH}{\diagdown CH_2-COOH}$$

are effective for bonding of ivory.

These carboxyl group-containing acrylate compounds are considerably improved in the adhesive force over the known adhesives, but these acrylate compounds are still insufficient in the bonding capacity in the wet state, the long-period water resistance and the resistance to repeated heating in water. Accordingly, it is desired that these insufficient properties will be improved.

SUMMARY OF THE INVENTION

It is therefore a primary object of the present invention to provide a novel adhesive compound having a high adhesive force.

Another object of the present invention is to provide a novel compound having a durable adhesiveness.

Still another object of the present invention is to provide a novel compound valuable as a dental adhesive and an adhesive composition comprising this novel compound.

Other objects of the present invention will become apparent from the following detailed description.

In accordance with the present invention, there is provide an acrylate compound represented by the following general formula:

$$(CH_2=\underset{\underset{\displaystyle R_1}{|}}{C}-COO-R_2)_{\overline{n}}C\underset{\diagdown COOH}{\overset{\diagup (R_3)_{2-n}}{\diagup COOH}} \qquad (I)$$

wherein $R_1$ stands for a hydrogen atom or an alkyl group having 1 to 4 carbon atoms, $R_2$ stands for an alkylene group having 2 to 20 carbon atoms, $R_3$ stands for a hydrogen atom or an alkyl group having 1 to 20 carbon atoms when n is 1, and n is 1 or 2.

In accordance with another aspect of the present invention, there is provided an acrylate compound composition comprising (a) an acrylate compound represented by the above-mentioned general formula (I) and (b) at least one member selected from the group consisting of a vinyl monomer copolymerizable with the acrylate compound (a), (c) a polymerization catalyst and (d) a filler.

DETAILED DESCRIPTION OF THE PREFERRED EMBODIMENTS

Figure 1:
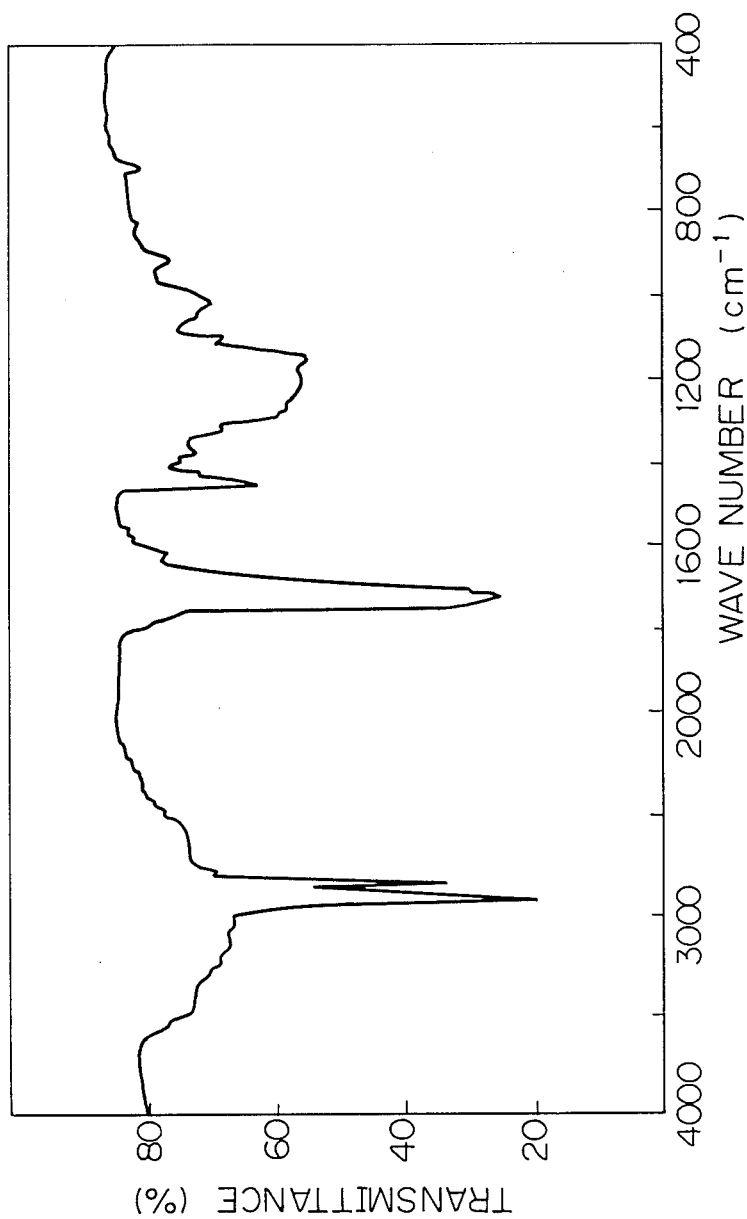
FIG. 1 shows the infrared absorption spectrum of an acrylate compound obtained in Example 1.

The compound provided according to the present invention is an acrylate compound represented by the following general formula:

$$(CH_2=\underset{\underset{\displaystyle R_1}{|}}{C}-COO-R_2)_{\overline{n}}C\underset{\diagdown COOH}{\overset{\diagup (R_3)_{2-n}}{\diagup COOH}} \qquad (I)$$

In the above general formula (I), $R_1$ stands for a hydrogen atom or an alkyl group having 1 to 4 carbon atoms. In view of the easiness of the industrial preparation, a hydrogen atom or a methyl or ethyl group is preferred. Of course, propyl and butyl groups may be similarly selected.

In the above general formula (I), $R_2$ stands for an alkylene group having 2 to 20 carbon atoms, preferably 4 to 12 carbon atoms. As preferred examples, there can be mentioned $-(CH_2)_{\overline{2}}$, $-(CH_2)_{\overline{3}}$, $-(CH_2)_{\overline{4}}$, $-(CH_2)_{\overline{5}}$, -continued $$-(-CH-CH_2-CH-)-, -(-CH_2-)_6, -(-CH-CH_2-CH_2-CH-)-,$$
$$\quad\quad |\quad\quad\quad\;|\quad\quad\quad\quad\quad\quad\quad\;|\quad\quad\quad\quad\quad\quad\quad\;|$$
$$\quad\; CH_3\quad\;CH_3\quad\quad\quad\quad\quad CH_3\quad\quad\quad\quad\quad CH_3$$

$$-(-CH_2-)_7, -(-CH_2-)_8, -(-CH_2-)_9, -(-CH_2-)_{10},$$

$$-(-CH_2-)_{11}\; and\; -(-CH_2-)_{12}.$$

In the above general formula (I), $R_3$ is present when n is 1. In this case, $R_3$ stands for a hydrogen atom or an alkyl group having 1 to 20 carbon atoms, preferably 1 to 4 carbon atoms. As preferred examples, there can be mentioned $$-CH_3, -C_2H_5, -C_3H_7, -CH\begin{matrix}CH_3\\ \\ CH_3\end{matrix}, -C_4H_9, -\underset{\underset{CH_3}{|}}{\overset{\overset{CH_3}{|}}{C}}-CH_3,$$

$-C_5H_{11}, -C_6H_{13}, -C_7H_{15}, -C_8H_{17}, -C_9H_{19}$ and $-C_{10}H_{21}$.

In the above general formula (I), n is 1 or 2, and it is generally preferred that n is 1.

Of the acrylate compounds represented by the general formula (I), ω-acryloxy-α,α-alkanedicarboxylic acids and ω-methacryloxy-α,α-alkanedicarboxylic acids are especially preferred. As specific examples, the following compounds can be mentioned:

$$CH_2=\underset{\underset{H}{|}}{C}-COO-(-CH_2-)_6-CH\begin{matrix}COOH\\ \\ COOH\end{matrix},$$

$$\left[CH_2=\underset{\underset{H}{|}}{C}-COO-(-CH_2-)_6-\right]_2 C\begin{matrix}COOH\\ \\ COOH\end{matrix},$$

$$CH_2=\underset{\underset{CH_3}{|}}{C}-COO-(-CH_2-)_6-CH\begin{matrix}COOH\\ \\ COOH\end{matrix},$$

$$\left[CH_2=\underset{\underset{CH_3}{|}}{C}-COO-(-CH_2-)_6-\right]_2 C\begin{matrix}COOH\\ \\ COOH\end{matrix},$$

$$CH_2=\underset{\underset{CH_3}{|}}{C}-CCO-(-CH_2-)_8-CH\begin{matrix}COOH\\ \\ COOH\end{matrix},$$

$$CH_2=\underset{\underset{H}{|}}{C}-COO-(-CH_2-)_{10}-CH\begin{matrix}COOH\\ \\ COOH\end{matrix},$$

$$\left[CH_2=\underset{\underset{H}{|}}{C}-COO-(-CH_2-)_{10}-\right]_2 C\begin{matrix}COOH\\ \\ COOH\end{matrix},$$

$$CH_2=\underset{\underset{CH_3}{|}}{C}-COO-(-CH_2-)_{10}-CH\begin{matrix}COOH\\ \\ COOH\end{matrix},$$

-continued $$CH_2=\underset{\underset{CH_3}{|}}{C}-COO(CH_2)_8CH\begin{matrix}COOH\\ \\ COOH\end{matrix},$$

$$\left[CH_2=\underset{\underset{CH_3}{|}}{C}-COO-(-CH_2-)_{10}-\right]_2 C\begin{matrix}COOH\\ \\ COOH\end{matrix},$$

$$CH_2=\underset{\underset{H}{|}}{C}-COO-(-CH_2-)_6-\underset{\underset{COOH}{\diagdown}}{\overset{\overset{CH_3}{\diagup}}{C}}\begin{matrix}COOH\\ \end{matrix},$$

$$CH_2=\underset{\underset{H}{|}}{C}-COO-(-CH_2-)_{10}-\underset{\underset{COOH}{\diagdown}}{\overset{\overset{CH_3}{\diagup}}{C}}\begin{matrix}COOH\\ \end{matrix},$$

$$CH_2=\underset{\underset{CH_3}{|}}{C}-COO-(-CH_2-)_6-\underset{\underset{COOH}{\diagdown}}{\overset{\overset{CH_3}{\diagup}}{C}}\begin{matrix}COOH\\ \end{matrix} \text{ and}$$

$$CH_2=\underset{\underset{CH_3}{|}}{C}-COO-(-CH_2-)_{10}-\underset{\underset{COOH}{\diagdown}}{\overset{\overset{CH_3}{\diagup}}{C}}\begin{matrix}COOH\\ \end{matrix}.$$

The acrylate compound represented by the general formula (I) is a colorless or light-yellow transparent liquid.

The acrylate compound of the present invention can be identified by the following measurements.

(A) Measurement of Infrared Absorption Spectrum (IR)

When IR of the compound represented by the general formula (I) is measured, an absorption attributed to an aliphatic carbon-hydrogen bond is observed in the vicinity of 3000–2800 cm$^{-1}$, a strong absorption attributed to a carbonyl group is observed in the vicinity of 1800–1600 cm$^{-1}$ and an absorption attributed to a carbon-to-carbon double bond is observed in the vicinity of 1650–1620 cm$^{-1}$.

(B) Measurement of $^1$H-Nuclear Magnetic Resonance Spectrum ($^1$H-NMR) (tetramethylsilane as reference; measurement of δppm)

(1) A peak attributed to a proton of a methylene group or a methyl group appears in the vicinity of 0.8–2.0 ppm.

(2) In the case where $R_1$ in the general formula (I) is $CH_3$, a peak attributed to a proton of a methyl group appears in the vicinity of 1.9 ppm.

(3) In the case where $R_3$ in the general formula (I) is a hydrogen atom, a peak attributed to a proton of a methine group appears in the vicinity of 3.0–3.6 ppm.

(4) A peak attributed to a proton of a methylene group adjacent to $$-\overset{\overset{O}{\|}}{C}-O-$$

appears in the vicinity of 3.7–4.5 ppm.

(5) A peak attributed to a proton of a double bond appears in the vicinity of 5.2–6.6 ppm.

(6) A peak attributed to a proton of a carboxylic acid appears in the vicinity of 9–12 ppm. This peak disappears by substitution with deuterium.

(C) Mass Analysis

The molecular weight can be confirmed by using the electric field desorption ionization method (referred to as "MS-FD") as means of the mass analysis. Supposing that the molecular weight of the acrylate compound of the present invention is M, the peak of the molecule ion is observed at the position of $M^{\oplus}+1$ or $M^{\oplus}$.

(D) Elementary Analysis

The acrylate compound of the present invention can be identified by comparing the results of the analysis of carbon and hydrogen with the theoretical values calculated from the general formula (I).

According to the above-mentioned various measurement methods, the acrylate compound represented by the general formula (I) can be identified.

The process for the preparation of the acrylate compound represented by the general formual (I) is not particularly critical, but an optional process may be adopted. An industrially preferable example of the preparation process will now be described.

An acrylate compound of the general formula (I) is prepared by reacting a vinyl compound represented by the following general formula:

wherein $R_1$ is as defined above and Z stands for a hydroxyl group or a halogen atom,
with an alcohol compound represented by the following general formula:

wherein $R_2$ is as defined above and $R'_3$ is the same as $R_3$ or is a group of the formula $-R_2-OH$.

Any of known compounds represented by the general formula (II) can be used without any limitation. For example, when Z is a hydroxyl group, there can be mentioned acrylic acid, methacrylic acid and ethylacrylic acid, and when Z is a halogen atom, there can be mentioned acryloyl chloride, methacryloyl chloride, ethylacryloyl chloride, acryloyl bromide, methacryloyl bromide and ethylacryloyl bromide.

Any of alcohol compounds represented by the general formula (III) may be used irrespectively of the synthesis process. An example of the synthesis process will now be described.

Namely, an alcohol compound represented by the general formula (III) is prepared by reacting a malonic acid ester represented by the following general formula:

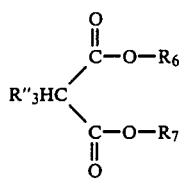

wherein $R''_3$ stands for a hydrogen atom or an alkyl group having 1 to 20 carbon atoms and $R_6$ and $R_7$, which may be the same or different, stand for an alkyl group having 1 to 20 carbon atoms or an aryl group,
with a halogenated alcohol compound represented by the following general formula:

$$HO-R_2-Z' \qquad (V)$$

wherein $R_2$ is as defined above and Z' stands for a halogen atom,
and hydrolyzing the reaction product.

Any of known malonic acid esters represented by the general formula (IV) can be used without any limitation. For example, there can be mentioned dimethyl malonate, diethyl malonate, dipropyl malonate, diisopropyl malonate, dibutyl malonate, di-tert-butyl malonate, diphenyl malonate, bismethylphenyl malonate, naphthyl malonate, dimethyl methylmalonate, diethyl methylmalonate, dimethyl ethylmalonate, diethyl ethylmalonate, diethyl propylmalonate, diethyl isopropylmalonate, diethyl butylmalonate, dimethyl butylmalonate, diethyl pentylmalonate, diethyl hexylmalonate, diethyl octylmalonate, diethyl nonylmalonate and diethyl decylmalonate.

Any of known halogenated alcohol compounds represented by the general formula (V) can be used without any limitation. Compounds of the general formula (V) in which Z' is a bromine atom or an iodine atom are especially preferred. As examples preferably used in the present invention, there can be mentioned 4-bromo-1-ethanol, 5-bromo-1-pentanol, 5-bromo-2-pentanol, 6-bromo-1-hexanol, 5-bromo-2-hexanol, 7-bromo-1-heptanol, 8-bromo-1-octanol, 9-bromo-1-nonanol, 10-bromo-1-decanol, 11-bromo-1-undecanol, 12-bromo-1-dodecanol, 6-iodo-1-hexanol and 10-iodo-1-decanol.

In the above-mentioned reaction, the molar ratio of the malonic acid ester of the general formula (IV) to the halogenated alcohol compound of the general formula (V) may be within the range of from 0.1 to 10. However, when an alcohol compound of the general formula (III) in which $R'_3$ is a hydrogen atom or an alkyl group is obtained, it is preferred that 1 mole of the halogenated alcohol compound be reacted with 1 mole of the malonic acid ester, and when an alcohol compound of the formula (III) in which $R'_3$ is $-R_2-OH$ (in which $R_2$ is as defined above) is obtained, it is preferred that 2 moles of the halogenated alcohol compound be reacted with 1 mole of the malonic acid ester. It is preferred that an alkali metal, an alkali metal hydrice or an alkali metal alcoholate, such as metallic sodium, metallic potassium, sodium hydride or sodium ethylate, be used in an amount of 1 to 2 moles per mole of the malonic acid ester for the above reaction. As the solvent, there may be used methanol, ethanol, isopropyl alcohol, 2-methyl-2-propanol, benzene and chloroform. The solvent may be used in an amount of at least 50% by volume, preferably 100 to 1000% by volume, based on the malonic acid ester. The reaction conditions are not particularly critical. The reaction temperature is at least 50° C., preferably 60° to 100° C., and the reaction time is at least 30 minutes, preferably 1 to 5 hours. After completion of the reaction, the reaction mixture is filtered and the solvent is distilled under reduced pressure, and hydroysis is carried out by an alkali, whereby an alcohol compound of the general formula (III) can be obtained. As the alkali, there is used an aqueous solution of an alkali metal hydroxide such as sodium hydroxide or potassium hydroxide having a concentration of 5 to 50% by weight, preferably 10 to 30% by weight, and the alkali is used in an amount of at least 2 moles, preferably 2.5 to 4 moles, per mole of the malonic acid ester. The hydrolysis temperature is not particularly critical, but it is preferred that the hydrolysis temperature be at least 50° C., especially 80° to 120° C. After completion of the hydrolysis, an alcohol formed as the by-product by the hydrolysis is distilled under reduced pressure. Then, an acid such as hydrochloric acid or sulfuric acid is added to the residue to reduce the pH value below 3. The reaction product is ordinarily solid or liquid, though the state differs according to the kind of $R_2$ or $R'_3$ in the general formula (III). In the case where the reaction product is solid, the reaction mixture is filtered and the solid is washed with water and dried under reduced pressure. In the case where the reaction product is liquid, the reaction product is isolated and recovered by extraction with a solvent separable from water, such as ethyl acetate, diethyl ether or methylisobutyl ketone.

The method for the reaction between the vinyl compound of the general formula (II) and the alcohol compound of the general formula (III) is not particularly critical. A preferred example of the reaction method will now be described.

More specifically, in the case where Z of the vinyl compound represented by the general formula (II) is a halogen atom, an acrylate compound of the general formula (I) is obtained by the following reaction. The vinyl compound of the general formula (II) is reacted in an equimolar amount or slight molar excess to the OH group of the alcohol compound of the general formula (III). The kind of the solvent is not particularly critical, but tetrahydrofuran, acetone, diethyl ether, dichloromethane, chloroform and benzene are generally used. The solvent is used in such an amount that the concentration of the alcohol compound of the general formula (III) is 0.1 to 50% by weight, preferably 1 to 10% by weight. When the vinyl compound is dropped, the reaction is carried out at a temperature lower than 30° C., preferably under ice cooling, and after completion of dropping of the vinyl compound, the reaction is carried out at a temperature lower than 70° C., preferably 10° to 40° C. It is preferred that this reaction be carried out in the presence of a base such as trimethylamine, triethylamine or pyridine. The base is preferably added in an equimolar amount or slight molar excess to the vinyl compound. It also is preferred that a small amount of a polymerization inhibitor such as hydroquinone, hydroquinone monomethyl ether or butylhydroxytoluene be added. After completion of the reaction, the salt formed as the by-product is removed by filtration and then, the solvent is distilled under reduced pressure, whereby the acrylate compound can be isolated and recovered. Preferably, the so-obtained product is dissolved in a solvent such as dichloromethane, chloroform, benzene, toluene, n-hexane or cyclohexane, the solution is washed with a dilute aqueous soluiton of hydrochloric acid and then washed with water 2 to 5 times, and the solvent is distilled under reduced pressure, whereby the product is purified.

In the case where Z of the vinyl compound represented by the general formula (II) is a hydroxyl group, the acrylate compound of the present invention can be obtained by reacting this vinyl compound with the alcohol compound represented by the general formula (III) in the following manner. Namely, the alcohol compound of the general formula (III) and the vinyl compound of the general formula (II) are subjected to dehydration reaction, whereby the acrylate compound of the present invention can be obtained. It is preferred that the reaction is carried out in the presence of an acid catalyst. As the acid catalyst, there are preferably used p-toluene-sulfonic acid, benzenesulfonic acid and sulfuric acid. The amount of the catalyst is 0.1 to 20% by weight, preferably 1 to 10% by weight, based on the vinyl compound. As the method for removal of water, there may be adopted a method in which the removal is carried out under reduced pressure and a method in which the removal is carried out under reflux with benzene or toluene. The reaction conditions are not particularly critical, but the reaction temperature is preferably 50° to 120° C. It also is preferred that a small amount of a polymerization inhibitor such as hydroquinone or hydroquinone monomethyl ether is added. After completion of the reaction mixture, the reaction mixture is transferred to a separating funnel, a solvent such as benzene, toluene, chloroform or dichloromethane is added, neutralizing washing is carried out by using an aqueous solution of sodium carbonate or sodium hydrogencarbonate, washing is further conducted with dilute hydrochloric acid and water, and the solvent is distilled under reduced pressure, whereby an acrylate compound represented by the general formula (I) can be isolated and recovered.

The acrylate compound represented by the general formula (I) according to the present invention has an excellent adhesiveness. Accordingly, the acrylate compound of the present invention is preferably used as an adhesive in combination with other copolymerizable vinyl monomer. Various embodiments may be considered for using the acrylate compound of the present invention as an adhesive. In general, however, the following embodiments are preferred.

More specifically, in accordance with one preferred embodiment of the present invention, there is provided (A) an acrylate compound composition comprising (a) 1 to 50% by weight of an acrylate compound represented by the general formula (I) and (b) 99 to 50% by weight of other vinyl monomer copolymerizable with said acrylate compound.

In accordance with another embodiment of the present invention, there is provided (B) an acrylate compound composition comprising (a) 1 to 50% by weight of an acrylate compound represented by the general formula (I), (b) 99 to 50% by weight of other vinyl monomer copolymerizable with said acrylate compound and (d) 5 to 500% by weight of a filler.

When the above-mentioned composition (A) or (B) is used as an adhesive, it is necessary that (c) a polymerization catalyst should be incorporated in an amount of 0.05 to 5% by weight based on the total amount of the acrylate compound (a) and the copolymerizable vinyl monomer (b).

Any of vinyl monomers copolymerizable with the acrylate compound (a) may be used as the copolymerizable vinyl monomer (b). When the composition (A) or (B) is used in the dental field, an acrylate monomer different from the acrylate compound (a) is used. The foregoing acrylate monomers may be used without any particular limitation. Vinyl monomers copolymerizable with the acrylate compound (a), which are preferably used, are described below.

(1) Vinyl monomers represented by the following general formula:

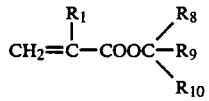  (VI)

wherein $R_1$ is as defined above, and $R_8$, $R_9$ and $R_{10}$, which may be the same or different, stand for a hydrogen atom or an alkyl group having 1 to 12 carbon atoms, which is unsubstituted or substituted with a hydroxyl group and/or an epoxy group.

(2) Vinyl monomers represented by the following general formula:

(VII)

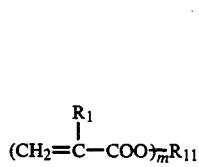

wherein $R_1$ is as defined above, m is a number of from 2 to 4, and when m is 2, $R_{11}$ stands for an alkylene group having 2 to 10 carbon atoms or a group

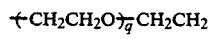

(in which q is an integer of from 1 to 9), when m is 3, $R_{11}$ stands for

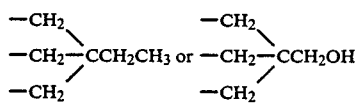

and when m is 4, $R_{11}$ stands for

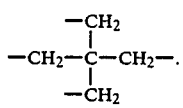

(3) Vinyl monomers represented by the following general formula:

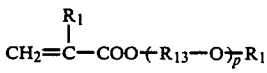  (VIII)

wherein $R_1$ is as defined above, $R_{13}$ stands for an alkylene group having 2 to 4 carbon atoms and p is a number of from 1 to 3.

(4) Vinyl monomers represented by the following general formula:

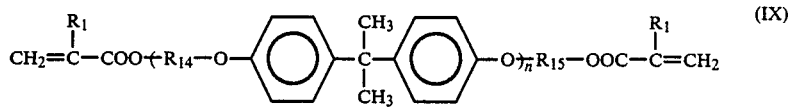  (IX)

wherein $R_1$ is as defined above, $R_{14}$ and $R_{15}$, which may be the same or different, stand for an alkylene group having 3 to 4 carbon atoms, which is substituted with a hydroxyl group, and n is 1 or 2.

(5) Vinyl monomers represented by the following general formula:

(X)

wherein $R_1$ is as defined above, l is a number of from 0 to 2, k is a number of from 0 to 2 and n is 1 or 2.

(6) Vinyl monomers represented by the following general formula:

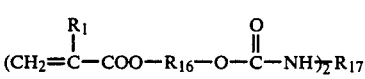  (XI)

wherein $R_1$ is as defined above, $R_{16}$ stands for an alkylene group having 2 to 4 carbon atoms and $R_{17}$ stands for an alkylene group having 4 to 12 carbon atoms.

As specific preferred examples of the vinyl monomer, the following compounds can be mentioned:

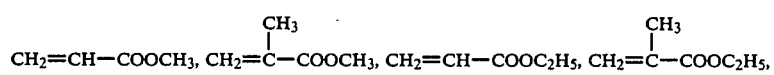

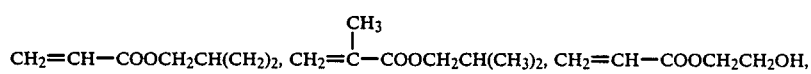

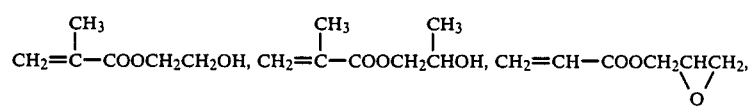

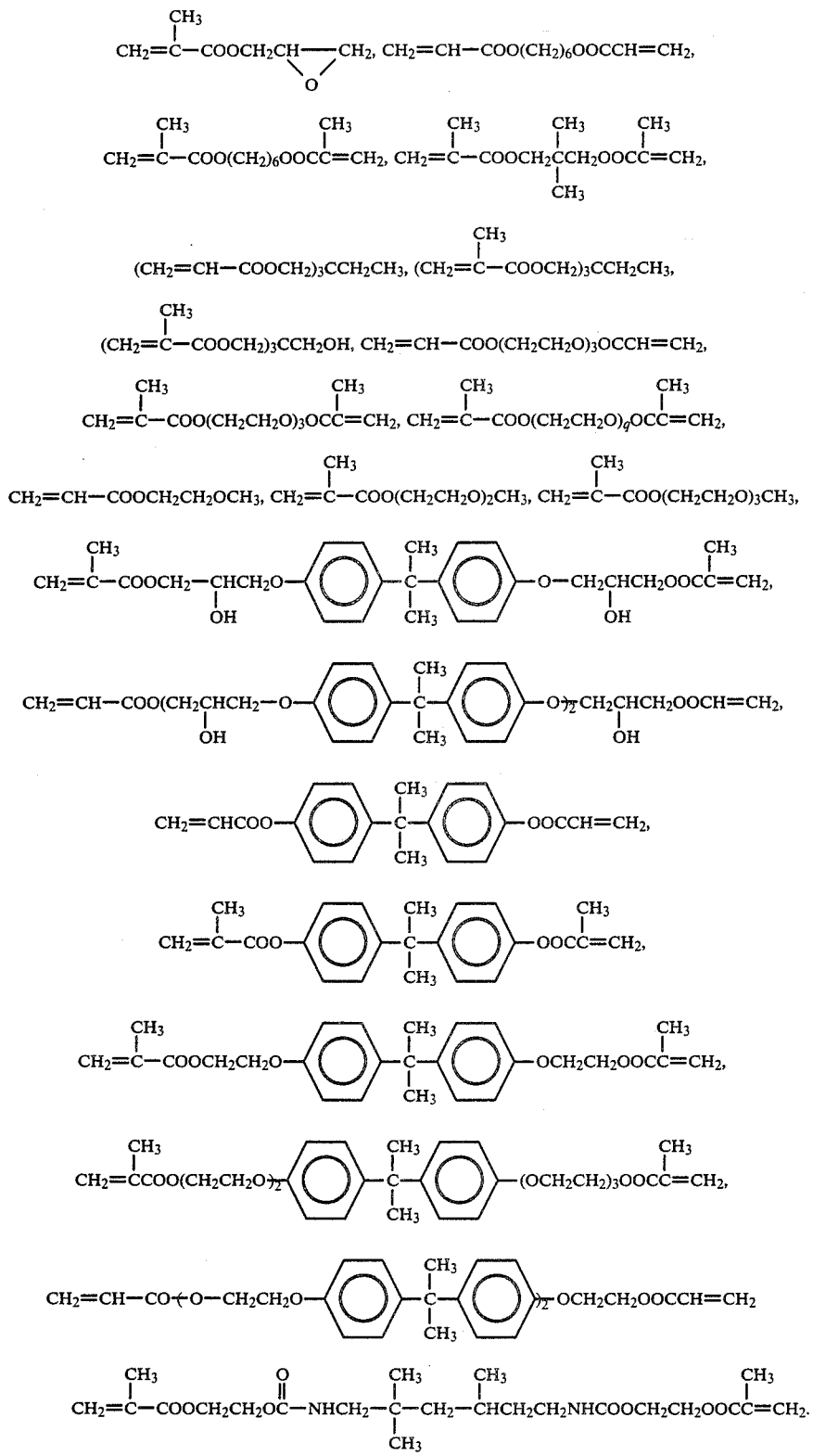

The vinyl monomer represented by the general formula (VI) or (VII) may be singly copolymerized with the acrylate compound represented by the general formula (I), but in case of the vinyl monomer represented by the general formula (VIII), (IX), (X) or (XI), it is often preferred that the vinyl monomer be used in combination with the vinyl monomer of the general formula (VI) or (VII) and copolymerized with the acrylate compound of the general formula (I). For example, good results are obtained when

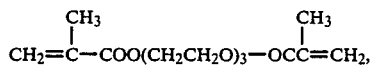

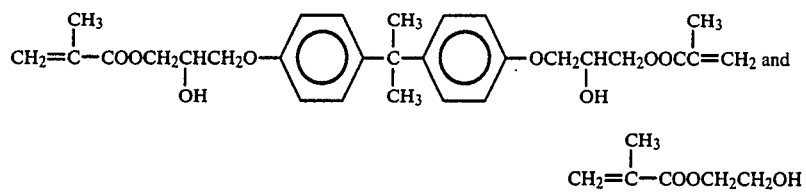

are mixed with the acrylate compound represented by the general formula (I), or when

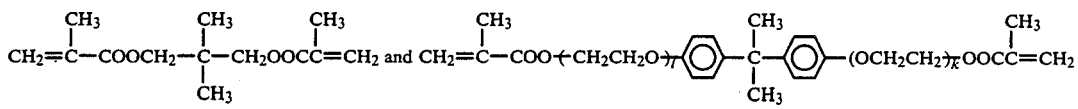

wherein l and k are selected from 1 and 2, and the compound is generally in the form of a mixture of a plurality of compounds of the above formula and in a typical instance, the mean value of (l+k) is 2.6, are mixed with the acrylate compound represented by the general formula (I).

As specific examples of copolymerizable vinyl monomers preferably used in the present invention, there can be mentioned methyl (meth)acrylate, ethyl (meth)acrylate, n-propyl (meth)acrylate, isopropyl (meth)acrylate, n-butyl (meth)acrylate, isobutyl (meth)acrylate, n-hexyl (meth)acrylate, 2-ethylhexyl (meth)acrylate, tridecyl (meth)acrylate, stearyl (meth)acrylate, 2-hydroxyethyl (meth)acrylate, 2-hydroxypropyl (meth)acrylate, glycidyl (meth)acrylate, methoxydiethylene glycol (meth)acrylate, ethylene glycol di(meth)acrylate, diethylene glycol di(meth)acrylate, triethylene glycol di(meth)acrylate, tetraethylene glycol di(meth)acrylate, propylene glycol di(meth)acrylate, 1,3-butane-diol di(meth)acrylate, 1,4-butane-diol di(meth)acrylate, 1,6-hexane-diol di(meth)acrylate, neopentyl glycol di(meth)acrylate, 1,10-decane-diol di(meth)acrylate, bisphenol A di(meth)acrylate, 2,2-bis((meth)acryloyloxypolyethoxyphenyl)-propane, 2,2'-bis(4-(3-methacryloyloxy-2-hydroxypropoxy)phenyl)propane, trimethylolpropane (methy)acrylate, trimethylolethane tri(meth)acrylate, tetramethylmethane tetra(meth)acrylate and di(methacryloxy)trimethylhexamethylene diurethane.

As the filler (d), known organic polymers and inorganic substances customarily used for adhesives may be used without any particular limitation. An appropriate filler is selected and used according to the kind of an object to be bonded, or in case of some objects to be bonded, a filler may not be incorporated. Generally, by incorporation of the filler, the mechanical strength and water resistance can be improved, and the fluidity and coating property of the adhesive can be controlled. Therefore, good results are generally obtained when the filler is incorporated.

As preferred examples of the filler, there can be mentioned inorganic substances such as quartz, amorphous silica, a compound of silica with titania or zirconia, clay, aluminum oxide, talc, mica, kaolin, barium glass, barium sulfate, zirconium oxide, tatanium oxide, silicon nitride, aluminum nitride, titanium nitride, silicon carbide, boron carbide, calcium carbonate, hydroxyapatite and calcium phosphate, organic polymers and oligomers such as polymethyl methacrylate, polyethyl methacrylate, polyvinyl chloride, polystyrene, polyesters and nylons, and organic-inorganic composite fillers. It is generally preferred that the inorganic filler be used after it has been treated with a silane coupling agent such as γ-methacryloyloxypropyltrimethoxysilane or vinyltriethoxysilane.

Of the above-mentioned fillers, polymethyl methacrylate, polyethyl methacrylate, a copolymer comprising methyl methacrylate or ethyl methacrylate as one component, amorphous silica, quartz, a compound of silica with titania or zirconia, titania, barium sulfate, hydroxy apatite and barium glass are especially preferred for adhesives to be used in the dental field.

As pointed out hereinbefore, a polymerization catalyst is generally incorporated in the composition (A) or (B). An appropriate compound or an appropriate combination of a plurality of compounds is selected as the polymerization catalyst according to the polymerization method. Preferred examples will now be described.

(1) Heat Polymerization

A polymerization catalyst capable of generating a radical under heating is generally used. Typically, peroxides and azo compounds are used. Known peroxides or azo compounds may be used without any particular limitation. As the peroxide, there can be mentioned diacyl peroxides such as dibenzoyl peroxide, 2,4-dichlorobenzoyl peroxide, dilaurolyl peroxide, dioctanoyl peroxide and decanoyl peroxide, hydroperoxides such as cumene hydroperoxide and t-butyl hydroperoxide, and ketone peroxides such as cyclohexanone peroxide and methylethylketone peroxide. As the azo compound, there are preferably used 2,2'-azobisisobutyronitrile, 4,4'-azobis(4-cyanovaleric acid) and 2,2'-azobis(2,4-valeronitrile).

The catalyst is incorporated in an amount of 0.1 to 5% by weight, preferably 0.2 to 2% by weight, based on the amount of the total monomers. The polymerization temperature differs according to the kind of the catalyst used, but it is generally preferred that the polymerization temperature is 40° to 150° C., especially 50° to 130° C.

(2) Photo-polymerization

A polymerization catalyst capable of generating a radical under irradiation with light, that is, a photo-sensitizer, is used. Various photo-sensitizers are known, and these known photo-sensitizers may be used without any particular limitation in the present invention. As preferred examples, there can be mentioned α-diketones such as diacetyl, acetylbenzoin, benzyl, 2,3-pentadione, 2,3-octadione, 4,4'-dimethoxybenzyl, α-naphthyl, β-naphthyl, 4,4'-oxybenzyl, camphorquinone, 9,10-phenanthrenequinone and acenaphthenequinone, benzoin alkyl ethers such as benzoin methyl ether, benzoin ethyl ether and benzoin propyl ether, thioxanthone compounds such as 2,4-diethoxythioxanthone and methylthioxanthone, and benzophenone derivative such as benzophenone, p,p'-dimethylaminobenzophenone and p,p'-methoxybenzophenone.

It is preferred that the photo-sensitizer be incorporated in an amount of 0.05 to 5% by weight, especially 0.1 to 2% by weight, based on the amount of the total monomers.

When photo-curing is carried out, a curing promotor can be added simultaneously with the photo-sensitizer. As the curing promotor, there are preferably used amine compounds such as dimethylparatoluidine, N,N'-dimethylbenzylamine, N-methyldibutylamine and dimethylaminoethyl methacrylate, phosphite compounds such as dimethyl phosphite and dioctyl phosphite, cobalt compounds such as cobalt naphthenate, and barbituric acid compounds such as barbituric acid, 5-ethylbarbituric acid and 2-thiobarbituric acid. It is preferred that the amount added of the curing promotor be 0.05 to 5% by weight, especially 0.1 to 1% by weight.

The photo-curing is accomplished by irradiation with ultraviolet rays by a high pressure, medium pressure or low pressure mercury lamp or with visible rays by a halogen lamp or xenon lamp.

(3) Room Temperature Polymerization

In case of the room temperature polymerization, a peroxide is used as the polymerization catalyst. However, when a peroxide alone is used, a strong bonding force cannot be obtained by the room temperature polymerization, and hence, the peroxide is used in combination with an amine or amine salt and an organic sulfinic acid salt.

The kinds of the peroxide, the amine or its salt and the sulfinic acid salt are not particularly critical. However, as the organic peroxide, there are preferably used diacyl peroxides such as dibenzoyl peroxide, di-p-chlorobenzoyl peroxide and dilauroyl peroxide.

In view of the curing speed, a secondary amine or tertiary amine having an amino group bonded to an aryl group is preferably used as the amine. For example, there can be mentioned N,N'-dimethylaniline, N,N'-dimethyl-p-toluidine, N-methyl-N'-β-hydroxyethylaniline, N,N'-di(β-hydroxyethyl)aniline, N,N'-di(β-hydroxyethyl)-p-toluidine, N-methylaniline and N-methyl-p-toluidine. These amines may be in the form of salts with hydrochloric acid, acetic acid, phosphoric acid or an organic acid.

In view of the stability of the curing agent, an alkali metal salt, alkaline earth metal salt or amine salt of an arylsulfinic acid is preferred as the sulfinic acid salt. For example, there can be mentioned sodium benzene-sulfinate, calcium benzene-sulfinate, strontium benzene-sulfinate, ammonium benzene-sulfinate, triethylammonium benzene-sulfinate, N,N'-dimethyl-p-toluidine benzene-sulfinate and alkaline earth metal salts of p-toluene-sulfinic acid, β-naphthalene-sulfinic acid and styrene-sulfinic acid.

In the above-mentioned polymerization catalyst, it is preferred that the amount used of the peroxide and amine be 0.05 to 5% by weight, especially 0.1 to 2% by weight, based on the total monomers, and it also is preferred that the amount used of the organic sulfinic acid salt is 0.05 to 2% by weight, especially 0.1 to 0.9% by weight, based on the total monomers.

The adhesive of the present invention can be used in the form of a one-pack type adhesive or a two-pack type adhesive according to the intended use and the composition.

In case of the room temperature polymerization, if all the components of the polymerization catalyst are contained in one pack, the polymerization starts. Accordingly, in principle, the components of the polymerization catalysts are contained in two different packs, and when the adhesive is used, necessary amounts of the components are taken out from the packs and are mixed to form an adhesive. The adhesive of this type can be treated as in case of known adhesives.

It is preferred that a small amount of a polymerization inhibitor such as hydroquinone, hydroquinone monomethyl ether or butylhydroxytoluene is added to the adhesive composition of the present invention according to need.

Except the above-mentioned two-pack type adhesive, the acrylate compound composition of the present invention may be stored in one pack after the components (a) through (c) or (a) through (d) have been appropriately mixed. The mixing method is not particularly critical. For example, before packing the respective components are mixed by a kneader, a ball mill, a crusher or a V-blender. Alternately, the respective components are separately charged in a pack.

An organic solvent can be added to the composition of the present invention according to need. An easily volatile organic solvent such as acetone, dichloromethane, chloroform or ethanol is preferred as the organic solvent.

As illustrated in the examples given hereinafter, the acrylate compound represented by the general formula (I) has a very high adhesiveness and is excellent in the durability. Accordingly, an adhesive comprising this acrylate compound as one component can be used for bonding metals, ceramic materials, hard tissues of a human body such as teeth and bones, and organic polymeric materials.

The adhesive composition of the present invention is improved in the bonding strength, the water resistance and the resistance to repeated heating in water over known adhesive compositions. Accordingly, the adhesive composition is very important and valuable as a novel adhesive in all the kinds of bonding.

The present invention will now be described in detail with reference to the following examples that by no means limit the scope of the invention.

The following abbreviations are used in the examples.
D-2.6 E:

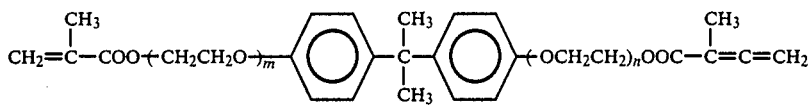

in which the mean value of m+n is 2.6.
3 G: triethylene glycol dimethacrylate
HEMA: 2-hydroxyethyl methacrylate
Bis-GMA: 2,2-bis(4-(3-methacryloyloxy-2-hydroxypropoxy)-phenyl)propane
NPG: neopentyl glycol dimethacrylate
BPO: dibenzoyl peroxide
AIBN: 2,2'-azobisisobutyronitrile
BHT: butylhydroxytoluene
HQME: hydroquinone monomethyl ether
UDMA: di(methacryloxyethyl)trimethylhexamethylenediurethane
HD: 1,6-hexane-diol dimethacrylate
PMMA: polymethyl methacrylate
PEMA: polyethyl methacrylate

EXAMPLE 1

A 300-ml three-neck flask equipped with a dropping funnel and a cooling tube was charged with 33.8 g of diethyl malonate and 150 ml of ethanol, and 4.85 of metallic sodium was added under ice cooling and the mixture was stirred until a homogenous solution was formed. Then, 50.0 g of 10-bromo-1-decanol was dropped through the dropping funnel and the solution was heated at 80° C. for 3 hours.

The solution was transferred to an eggplant type flask having a capacity of 500 ml and ethanol was distilled under reduced pressure. Then, 120 ml of an aqueous solution of NaOH having a concentration of 20% by weight was added and the mixture was heated at 100° C. for 2 hours, and 130 ml of 6N hydrochloric acid was dropped to adjust the pH value of the solution to about 2. The formed solid was recovered by filtration, washed with water and dissolved in acetone, and water was removed by anhydrous sodium sulfate and anhydrous magnesium sulfate. Then, acetone was removed by distillation under reduced pressure at room temperature.

A 300-ml three-neck flask equipped with dropping funnel was charged with 10 g of the so-obtained solid, 4.27 g of triethylamine, 20 mg of hydroquinone and 200 ml of tetrahydrofuran, and 4.42 ml of methacryloyl chloride was dropped through the dropping funnel under ice cooling. The mixture was allowed to stand at room temperature with stirring overnight, and the mixture was filtered through a filter having a mesh size of 0.5 μm to remove triethylamine hydrochloride salt. The obtained solution was subjected to distillation under reduced pressure at room temperature to remove tetrahydrofuran. The recovered product was purified by extraction with 200 ml of dichloromethane and 100 ml of 0.1N hydrochloric acid. The dichloromethane layer was concentrated to obtain 8.5 g of a viscous, light yellow liquid. From various measurement results described below, it was confirmed that the isolated product was an acrylate compound represented by the following formula:

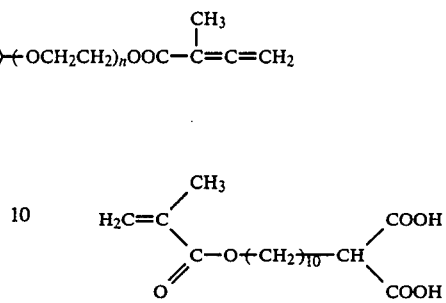

(a) The IR chart was as shown in FIG. 1 of the accompanying drawings.

The absorption attributed to the aliphatic carbon-hydrogen bond was observed at 3000–2800 cm$^{-1}$, the absorption attributed to the carbonyl group was observed at 1800 to 1640 cm$^{-1}$, and the absorption attributed to the carbon-to-carbon double bond was observed at 1640 to 1620 cm$^{-1}$.

Figure 2:
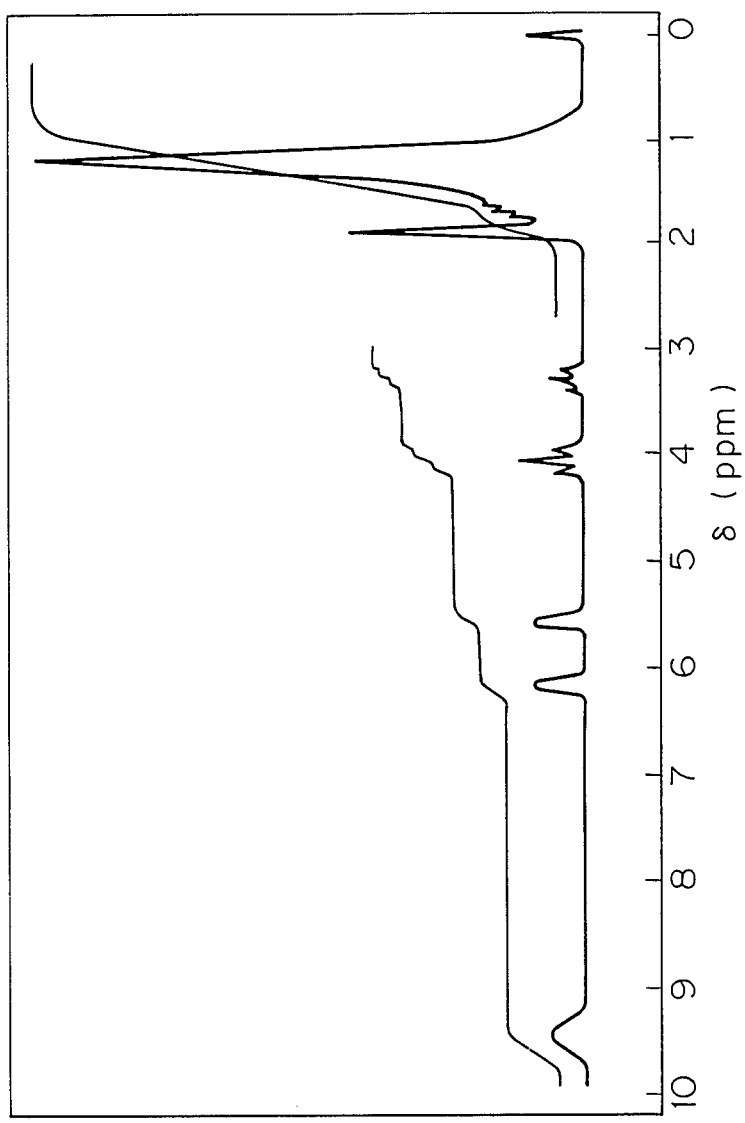
FIGS. 2, 3 and 4 show the $^1$H-nuclear magnetic resonance absorption spectra of acrylate compounds obtained in Examples 1, 4 and 5, respectively.

(b) The $^1$H-NMR chart (tetramethylsilane as reference, δ ppm, 60 MHz) was as shown in FIG. 2 of the accompanying drawings. A singlet of two protons of the carboxylic acid appeared at 9.5 ppm (lost by substitution with deuterium), doublets of two protons of the double bond appeared at 5.6 ppm and 6.2 ppm, respectively, a triplet of two protons of the methylene group adjacent to the ester bond appeared at 4.3–3.9 ppm, a triplet of one proton of the methine group appeared at 3.55–3.15 ppm, a singlet of three protons of the methyl group appeared at 1.9 ppm, a broad singlet of 18 protons of the methylene groups appeared with 1.3 ppm being as the center.

(c) From the results of the measurement of the mass spectrum by the mass analysis (MS-FD), it was confirmed that the peak of M$^{\oplus}$+1 appeared at m/e 329.

(d) The elementary analysis values were 62.05% of C 8.61% of H, which were well in agreement with the theoretical values, that is, 62.17% of C and 8.59% of H.

EXAMPLE 2

A 300-ml three-neck flask equipped with a dropping funnel and a cooling tube was charged with 33.8 g of diethyl malonate and 150 ml of ethanol, and 4.85 g of metallic sodium was added under ice cooling and stirring was conducted until a homogeneous solution was formed. Then, 50 g of 10-bromo-1-decanol was added and the solution was heated at 70° C. for 5 hours.

The solution was transferred to an eggplant type flask having a capacity of 500 ml and 120 ml of an aqueous solution of NaOH having a concentration of 20% by weight was added and ethanol was distilled while the hydrolysis was carried out at 100° C. for 2 hours. Then, 130 ml of 6N hydrochloric acid was dropped to adjust the pH value of the solution to about 2. The formed solid was recovered by filtration using a glass filter and washed with water.

Then, a 300-ml three-neck flask was charged with 30 g of the so-obtained solid, 60 g of methacrylic acid, 1 g of p-toluene-sulfonic acid and 0.1 g of HQME, and dehydration reaction was carried out at 80° C. for 3 hours under reduced pressure (100–200 mmHg) while blowing dry air into the flask. The resulting liquid was transferred to a separating funnel having a capacity of 1 liter, and 200 ml of dichloromethane and 200 ml of water were added and sodium hydrogencarbonate was added little by little to adjust the pH value to about 8. The dichloromethane layer was washed with water 2 or 3 times. Then, 1N hydrochloric acid was added to adjust the pH value to about 2. Water washing was further conducted and concentration was carried out to obtain the same acrylate compound as obtained in Example 1.

EXAMPLE 3

A 300-ml flask equipped with a dropping funnel and a cooling tube was charged with 44.2 g of diethyl malonate and 100 ml of ethanol, and 6.4 g of metallic sodium was added under ice cooling and stirring was conducted until a homogeneous solution was formed. Then, 50.0 g of 6-bromo-hexanol was dropped and the solution was heated at 70° C. for 5 hours.

The solution was transferred to an eggplant type flask having a capacity of 500 ml, and 100 ml of an aqueous solution of NaOH having a concentration of 30% by weight was added and the mixture was heated at 110° C. for 1 hour. After cooling, 12N hydrochloric acid was dropped to adjust the pH value below 2 and the majority of ethanol was removed by distillation under reduced pressure. The solution was transferred to a separating funnel having a capacity of 500 ml and 200 ml of ethyl acetate was added, and water washing was carried out 3 times and the ethyl acetate layer was dehydrated with anhydrous sodium sulfate and anhydrous magnesium sulfate. The solvent was removed by distillation under reduced pressure to obtain 33.8 g of a malonic acid compound.

The malonic acid compound was reacted with methacryloyl chloride in the same manner as described in Example 1 to obtain the following acrylate compound:

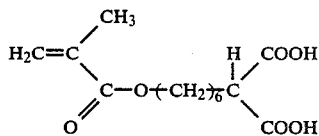

(a) IR

The absorption attributed to the aliphatic carbon-hydrogen bond was observed at 3000–2800 cm$^{-1}$, the absorption attributed to the carbonyl group was observed at 1800–1640 cm$^{-1}$, and the absorption attributed to the carbon-to-carbon double bond was observed at 1640–1620 cm$^{-1}$.

(b) $^1$H-NMR (tetramethylsilane as reference, δppm, 60 MHz)

The spectrum was the same as the spectrum of FIG. 2 obtained in Example 1 except that a broad singlet of 10 protons of the methylene groups appeared with 1.30 ppm being as the center.

(c) Mass Analysis (MS-FD)

In the mass spectrum, the peak of M$^\oplus$+1 appeared at m/e 273.

(d) Elementary Analysis Values

The elementary analysis values were 57.20% of C and 7.45% of H, and they were well in agreement with the theoretical values, that is, 57.34% of C and 7.40% of H.

EXAMPLE 4

The following acrylate compound was prepared in the same manner as described in Example 1 except that 36.7 g of diethyl methyl malonate, 50.0 g of 10-bromo-1-decanol and 4.85 g of metallic sodium were used as the starting compounds:

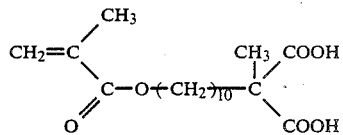

(a) IR

The absorption attributed to the aliphatic carbon-hydrogen bond was observed at 3000–2800 cm$^{-1}$, the absorption attributed to the carbonyl group was observed at 1800–1640 cm$^{-1}$, and the absorption attributed to the carbon-to-carbon double bond was observed at 1640–1620 cm$^{-1}$.

(b) $^1$H-NMR (tetramethylsilane as reference, δppm, 60 MHz)

Figure 3:
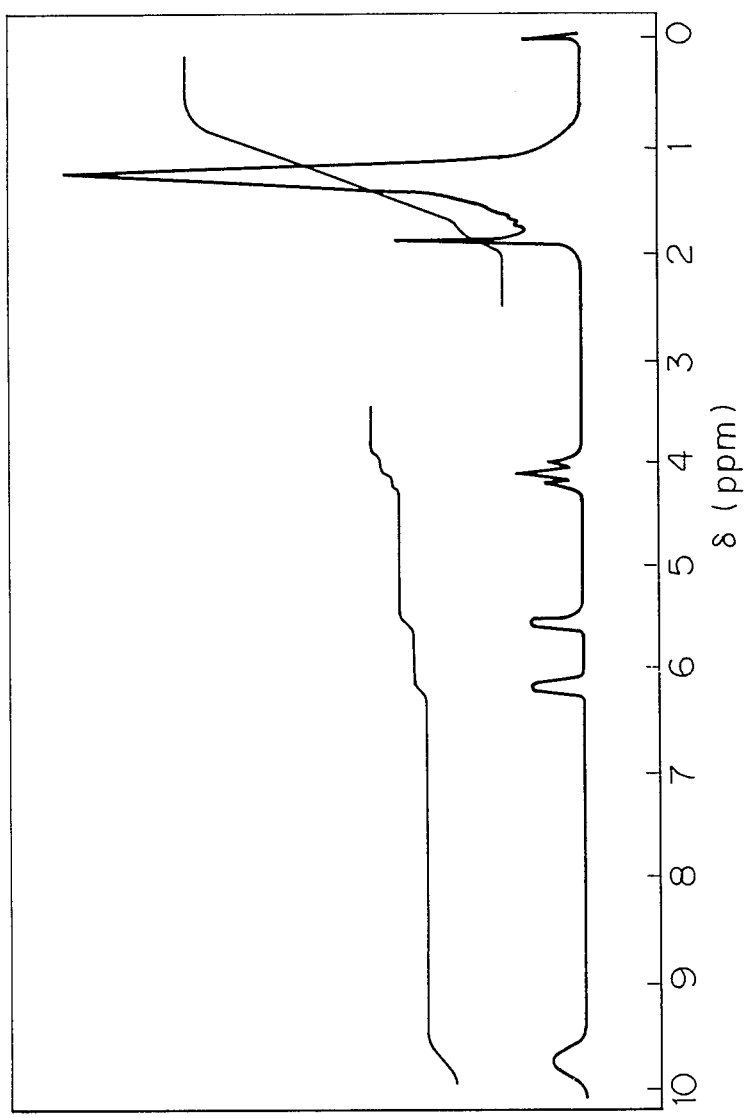

The $^1$H-NMR chart was as shown in FIG. 3 of the accompanying drawings. A singlet of two protons of the carboxylic acid appeared at 9.8 ppm (lost by substitution with deuterium), doublets of two protons of double bonds appeared at 5.6 ppm and 6.2 ppm, respectively, a triplet of two protons of the methylene group adjacent to the ester bond appears at 4.3–3.9 ppm, a singlet of three protons of the methyl group on the double bond appeared at 1.9 ppm, and a broad singlet of 21 protons of methyl groups on quaternary carbons and methylene groups appeared with 1.3 ppm being as the center.

(c) Mass Analysis (MS-FD)

In the mass spectrum, the peak of M$^\oplus$+1 appeared at m/e 343.

(d) Elementary Analysis Values

The elementary analysis values were 63.19% of C and 8.91% of H, and they were well in agreement with the theoretical values, that is, 63.13% of C and 8.83% of H.

EXAMPLE 5

A 300-ml three-neck flask equipped with a dropping funnel and a cooling tube was charged with 33.8 g of diethyl malonate and 150 ml of ethanol, and 4.85 g of metallic sodium was added under ice cooling and stirring was conducted until a homogeneous solution was obtained. Then, 50 g of 10-bromo-1-decanol was dropped through the dropping funnel and the solution was heated at 80° C. for 3 hours. After cooling, 4.85 g of metallic sodium was further added and dissolved in the solution. Then, 50 g of 10-bromo-1-decanol was dropped through the dropping funnel and the solution was heated at 80° C. for 5 hours. Then, the solution was treated in the same manner as described in Example 1 to obtain the following acrylate compound:

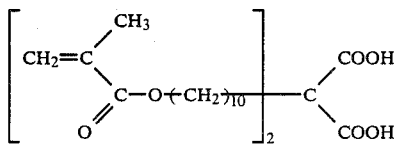

(a) IR

The absorption attributed to the aliphatic carbon-hydrogen bond was observed at 3000–2800 cm$^{-1}$, the absorption attributed to the carbonyl group was observed at 1800–1640 cm$^{-1}$, and the absorption attributed to the carbon-to-carbon double bond was observed at 1640 to 1620 cm$^{-1}$.

(b) $^1$H-NMR (tetramethylsilane as reference, δppm, 60 MHz)

Figure 4:
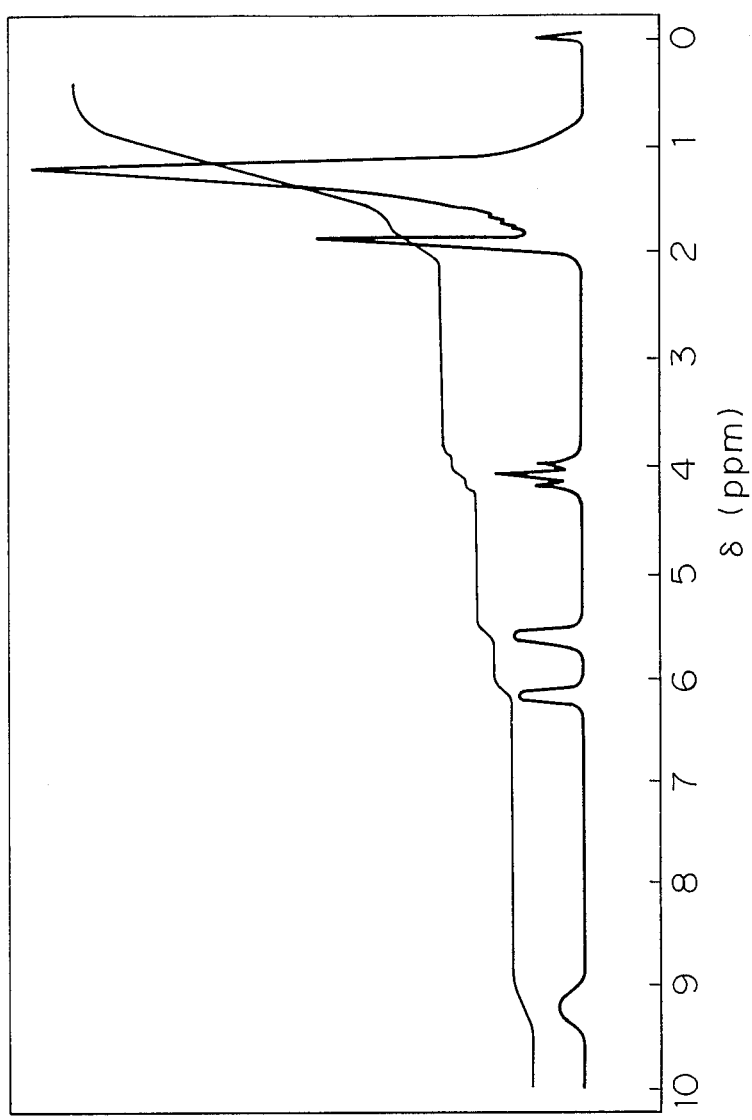

The $^1$H-NMR chart was as shown in FIG. 4 of the accompanying drawings. A singlet of two protons of the carboxylic acid appeared at 9.3 ppm (lost by substitution with deuterium), doublets of 4 protons of double bonds appeared at 5.6 ppm and 6.2 ppm, respectively, a triplet of 4 protons of methylene groups adjacent to the ester bond appeared at 4.3–3.9 ppm, a singlet of 6 protons of methyl groups appeared at 1.9 ppm, and a broad singlet of 36 protons of methylene groups appeared with 1.3 ppm being as the center.

(c) Mass Analysis (MS-FD)

In the mass spectrum, the peak of M$^\oplus$ + 1 appeared at m/e 554.

(d) Elementary Analysis Values

The elementary analysis values were 67.45% of C and 9.51% of H, and they were well in agreement with the theoretical values, that is, 67.36% of C and 9.48% of H.

EXAMPLE 6

Various acrylate compounds shown in Table 1 were synthesized by carrying out the reaction in the same manner as described in Example 1 or 5. Each compound was identified and confirmed by the methods described in Example 1.

Incidentally, $R_1$, $R_2$, $R_3$ and n in Table 1 are those of the following general formula:

TABLE 1

$$(CH_2=\overset{R_1}{\underset{|}{C}}-COO-R_2)_nC\overset{(R_3)_{2-n}}{\underset{COOH}{\diagdown COOH}}$$

| Run No. | $R_1$ | $R_2$ | $R_3$ | n | Composition Formula (molecular weight) | Elementary Analysis Values (% by weight) (theoretical values) C | H |
|---|---|---|---|---|---|---|---|
| 1 | H | $+CH_2)_4$ | H | 1 | $C_{10}H_{14}O_6$ (230.22) | 52.93 (52.17) | 6.40 (6.13) |
| 2 | H | $+CH-CH_2-CH_2-CH+$ <br> $\quad\|\quad\quad\quad\quad\|$ <br> $\quad CH_3\quad\quad\quad CH_3$ | H | 1 | $C_{12}H_{18}O_6$ (258.27) | 55.60 (55.81) | 6.98 (7.02) |
| 3 | $CH_3$ | $+CH-CH_2-CH+$ <br> $\quad\|\quad\quad\quad\|$ <br> $\quad CH_3\quad\quad CH_3$ | H | 1 | $C_{12}H_{18}O_6$ (258.27) | 55.73 (55.81) | 6.94 (7.02) |
| 4 | $CH_3$ | $+CH_2)_{12}$ | H | 1 | $C_{18}H_{30}O_6$ (342.43) | 63.02 (63.13) | 8.90 (8.83) |
| 5 | H | $+CH_2)_4$ | $CH_3$ | 1 | $C_{11}H_{16}O_6$ (244.24) | 54.15 (54.09) | 6.72 (6.60) |
| 6 | H | $+CH_2)_{12}$ | $CH_3$ | 1 | $C_{19}H_{32}O_6$ (356.46) | 63.93 (64.02) | 9.10 (9.05) |
| 7 | $CH_3$ | $+CH_2)_{10}$ | $C_3H_7$ | 1 | $C_{20}H_{34}O_6$ (370.49) | 64.75 (64.84) | 9.30 (9.25) |
| 8 | H | $+CH_2)_{10}$ | $CH\diagup^{CH_3}_{\diagdown CH_3}$ | 1 | $C_{19}H_{32}O_6$ (356.46) | 63.89 (64.02) | 9.01 (9.05) |
| 9 | H | $+CH_2)_{10}$ | $C_{10}H_{21}$ | 1 | $C_{26}H_{46}O_6$ (454.65) | 68.56 (68.69) | 10.11 (10.20) |
| 10 | $CH_3$ | $+CH_2)_6$ | $C_{10}H_{21}$ | 1 | $C_{23}H_{40}O_6$ (412.57) | 66.82 (66.96) | 9.69 (9.77) |
| 11 | H | $+CH_2)_6$ | — | 2 | $C_{21}H_{32}O_8$ (412.48) | 61.01 (61.16) | 7.79 (7.82) |
| 12 | H | $+CH_2)_{10}$ | — | 2 | $C_{29}H_{48}O_8$ (524.69) | 65.27 (66.38) | 9.11 (9.22) |
| 13 | $CH_3$ | $+CH_2)_4$ | — | 2 | $C_{18}H_{26}O_8$ (370.40) | 58.40 (58.37) | 7.16 (7.07) |

EXAMPLES 7 THROUGH 12 AND COMPARATIVE EXAMPLES 1 THROUGH 3

With respect to the acrylate compounds obtained in Examples 1 through 6, the adhesion strength was tested.

An adhesive composition shown in Table 2 was prepared.

TABLE 2

| Component | Amount (parts by weight) |
|---|---|
| D-2.6E | 40 |
| NPG | 30 |
| 3G | 20 |
| Acrylate compound | 10 |
| Silane-treated fine quartz powder | 100 |
| BPO | 2 |
| HQME | 0.05 |

The adhesion strength of the adhesive composition was measured according to the following procedures.

An Ni—Cr alloy having a length of 10 mm, a width of 10 mm and a thickness of 3 mm was polished by #1000 abrasive paper and then by 0.3 μm Al$_2$O$_3$. A sticky double-coated tape having a hole of a diameter of 5 mm and having a thickness of 50 μm was applied to the polished Ni—Cr alloy and the adhesive composition was coated on the hole. A stainless steel rod having a diameter of 8 mm and a length of 20 mm, which had been polished by #320 abrasive paper was pressed on the adhesive composition and the assembly was heated at 100° C. for 15 minutes. The adhesion strength of the bonded structure was measured just after cooling (AA), after immersion in water at 23° C. for 6 months (AB) and after 5000 times repetition of the heat treatment comprising immersion in water at 4° C. for 1 minute and immersion in water at 60° C. for 1 minute (AC). The obtained results are shown in Table 3.

Incidentally, the following compounds were used as the acrylate compound of the adhesive composition of the present invention.

The following compounds were used as the adhesive component of the comparative adhesive composition.

TABLE 3

| Example No. | Acrylate Compound | Adhesion Strength (AA) (kg/cm²) | Adhesion Strength (AB) (kg/cm²) | Adhesion Strength (AC) (kg/cm²) |
| --- | --- | --- | --- | --- |
| 7 | A | 356 | 348 | 331 |
| 8 | B | 330 | 329 | 309 |
| 9 | C | 338 | 320 | 305 |
| 10 | D | 342 | 334 | 321 |
| 11 | E | 326 | 305 | 295 |
| 12 | F | 310 | 312 | 297 |
| Comparative Example 1 | not added | 98 | 70 | 20 |
| Comparative Example 2 | R | 192 | 157 | 101 |
| Comparative Example 3 | S | 235 | 200 | 154 |

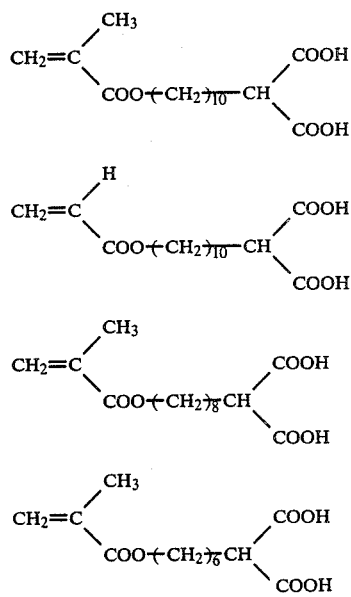

A

B

C

D

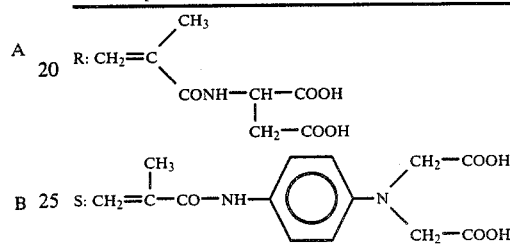

R

S

EXAMPLES 13 THROUGH 18

By using the acrylate compound A, adhesive compositions were prepared in the same manner as described in Examples 7 through 12 except that 2 parts by weight of a peroxide shown in Table 4 was used instead of BPO, and the adhesion strength was measured in the same manner as described in Examples 7 through 12 except that the heating temperature was changed according to the kind of the peroxide. The obtained results are shown in Table 4.

TABLE 4

| Example No. | Peroxide | Adhesion Strength (AA) (kg/cm²) | Adhesion Strength (AB) (kg/cm²) | Adhesion Strength (AC) (kg/cm²) | Heating Temperature (°C.) |
| --- | --- | --- | --- | --- | --- |
| 13 | decanoyl peroxide | 340 | 321 | 318 | 100 |
| 14 | lauroyl peroxide | 342 | 316 | 310 | 100 |
| 15 | methylethylketone peroxide | 325 | 308 | 297 | 120 |
| 16 | cyclohexanone peroxide | 321 | 300 | 286 | 120 |
| 17 | cumene hydroperoxide | 310 | 287 | 274 | 150 |
| 18 | t-butyl hydroperoxide | 308 | 281 | 269 | 150 |

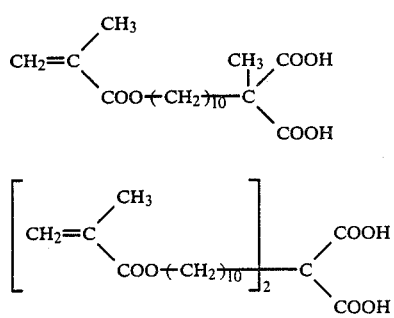

E

F

EXAMPLES 19 THROUGH 24 AND COMPARATIVE EXAMPLES 4 THROUGH 6

Adhesive compositions were prepared in the same manner as described in Examples 7 through 12 except that an azo compound shown in Table 5 was used instead of benzoyl peroxide and the bonding operation was carried out at 80° C. for 15 minutes. The adhesion strength was measured by the method described in Examples 7 through 12. The obtained results are shown in Table 5.

TABLE 5

| Example No. | Acrylate Compound | Azo Compound | Adhesion Strength (AA) (kg/cm²) | Adhesion Strength (AB) (kg/cm²) | Adhesion Strength (AC) (kg/cm²) |
| --- | --- | --- | --- | --- | --- |
| 19 | A | AIBN | 305 | 285 | 280 |
| 20 | B | 4-cyanovaleric acid | 296 | 280 | 275 |
| 21 | C | AIBN | 295 | 282 | 270 |
| 22 | D | azobisdimethyl-valeronitrile | 300 | 284 | 279 |
| 23 | E | AIBN | 293 | 276 | 271 |
| 24 | F | AIBN | 280 | 268 | 265 |
| Comparative Example | | | | | |
| 4 | not added | AIBN | 95 | 65 | 15 |
| 5 | R | AIBN | 180 | 135 | 86 |
| 6 | S | AIBN | 190 | 174 | 102 |

EXAMPLES 25 THROUGH 28

Adhesive compositions shown in Table 6 were prepared and the adhesion strength was measured by the method described in Examples 7 through 12. The obtained results are shown in Table 7.

TABLE 6

| Component | Amount (parts by weight) |
| --- | --- |
| HD | 50 |
| UDMA | 30 |
| Acrylate compound A | 20 |
| BPO | 1 |
| Filler | shown in Table 7 |

TABLE 7

| Example No. | Filler | Amount (parts by weight) of Filler | Adhesion Strength (AA) (kg/cm²) | Adhesion Strength (AB) (kg/cm²) | Adhesion Strength (AC) (kg/cm²) |
| --- | --- | --- | --- | --- | --- |
| 25 | quartz | 200 | 303 | 300 | 292 |
|  | barium sulfate | 50 | | | |
| 26 | silica-titania compound | 200 | 308 | 301 | 289 |
| 27 | silica-zirconia compound | 250 | 310 | 306 | 297 |
| 28 | PMMA | 50 | 290 | 283 | 274 |

EXAMPLES 29 THROUGH 39 AND COMPARATIVE EXAMPLES 7 THROUGH 9

The bonding strength between the adhesive composition and the dentine of a bovine tooth was measured according to the following method. A freshly extracted bovine front tooth stored in cold water was taken out from cold water just before the test, and the dentine was exposed under pouring of water in parallel to the lip surface by #800 emery paper. Then, compressed air was blown to the polished surface for 10 seconds to effect drying. A double-coated tape and paraffix wax having a hole having a diameter of 4 mm were fixed to the polished surface to form an imitation cavity.

An equal amount mixture of liquids I and II of an adhesive composition shown in Table 8 was coated on the tooth surface, and compressed air was blown to the surface to evaporate ethanol. Then, a kneaded commercially available composite resin (Palfique supplied by Tokuyama Soda) was filled in the cavity. After the composite resin was cured, the paraffin wax was removed and the test piece was stored in water at 37° C. for 24 hours. A metal attachment was attached to the test piece and the tensile adhesion strength was measured by a tensile tester at a crosshead speed of 10 mm/min. The obtained results are shown in Table 9.

TABLE 8

| | Component | Amount (parts by weight) |
| --- | --- | --- |
| Liquid I | Bis-GMA | 27 |
| | 3G | 43 |
| | HEMA | 20 |
| | acrylate compound | shown in Table 9 |
| | BPO | 1.0 |
| | HQME | 0.05 |
| Liquid II | ethanol | 100 |
| | sodium p-toluene-sulfinate | 0.8 |
| | N,N—diethanol-p-toluidine | 0.8 |

TABLE 9

| Example No. | Acrylate Compound | Amount (parts by weight) of Acrylate Compound | Adhesion Strength (kg/cm²) |
| --- | --- | --- | --- |
| 29 | A | 5 | 20 |
| 30 | A | 10 | 33 |
| 31 | A | 20 | 35 |
| 32 | A | 40 | 32 |
| 33 | B | 10 | 27 |
| 34 | C | 10 | 27 |
| 35 | D | 10 | 28 |
| 36 | D | 20 | 29 |
| 37 | D | 40 | 25 |
| 38 | E | 10 | 21 |
| 39 | F | 10 | 25 |
| Comparative Example | | | |
| 7 | not added | — | 0 (peeling on removal of paraffin wax) |
| 8 | R | 10 | 0 (peeling by immersion in water at 37° C.) |
| 9 | S | 10 | 0 (peeling by immersion in water |

TABLE 9-continued

| Acrylate Compound | Amount (parts by weight) of Acrylate Compound | Adhesion Strength (kg/cm²) at 37° C.) |
|---|---|---|

EXAMPLES 40 THROUGH 44

Adhesive compositions were prepared in the same manner as described in Examples 29 through 39 except that the amount added of the acrylate compound A was adjusted to 20 parts by weight in the liquid I and the sulfinic acid salt and amine in the liquid II were changed as shown in Table 10, and the adhesion strength was measured by the method described in Examples 29 through 39. The obtained results are shown in Table 10.

TABLE 10

| Example No. | Amine (parts by weight) | Sulfinic Acid Salt (parts by weight) | Adhesion Strength (kg/cm²) |
|---|---|---|---|
| 40 | N,N'—diethanol-p-toluidine (0.8) | sodium benzene-sulfinate (0.7) | 30 |
| 41 | N,N'—diethanol-p-toluidine (0.7) | ammonium benzene-sulfinate (0.6) | 25 |
| 42 | N,N'—dimethyl-p-toluidine (0.8) | sodium p-toluene-sulfinate (0.6) | 31 |
| 43 | N,N'—dimethyl-p-toluidine (0.7) | sodium benzene-sulfinate (0.7) | 32 |
| 44 | N,N'—dimethylaniline (1.0) | sodium p-toluene-sulfinate (0.8) | 26 |

EXAMPLES 45 THROUGH 54 AND COMPARATIVE EXAMPLES 10 THROUGH 12

The adhesion strengths of the adhesion composition of the present invention to the enamel of a bovine tooth and an Ni—Cr alloy were measured according to the following method. A freshly extracted bovine front tooth stored in cold water was taken out from cold water before the test, and the enamel was exposed under pouring of water in parallel to the lip surface by #800 emery paper. Then, the surface was etched for 30 seconds with an aqueous solution of phosphoric acid having a concentration of 37% by weight and washed with water, and compressed air was blown for about 10 seconds to effect drying. A double-coated tape having a hole of a diameter of 5 mm and having a thickness of 50 μm was applied to the tooth surface. An adhesive composition shown in Table 11 was coated in the hole and a stainless steel rod having a diameter of 8 mm and a length of 20 mm, the surface of which was roughened by 50 μm sand blast, was pressed in the hole. After the adhesive composition was cured, the bonded structure was immersed in water at 37° for 24 hours and the tensile adhesion strength was measured by a tensile tester at a crosshead speed of 10 mm/min.

In case of the adhesion strength of an Ni—Cr alloy, a test piece was prepared in the same manner as described in Examples 7 through 12, normal temperature curing was carried out at 23° C., the test piece was immersed in water at 37° C. for 24 hours, and the tensile strength was measured.

Incidentally, just before bonding, 1 part by weight of a liquid was mixed with 2 parts by weight of a powder for about 30 seconds.

TABLE 11

| | Component | Amount (parts by weight) |
|---|---|---|
| Liquid | D-2.6E | 40 |
| | NPG | 30 |
| | 3G | 20 |
| | Acrylate compound | shown in Table 12 |
| | BPO | 1 |
| | BHT | 0.05 |
| Powder | Silane-treated fine quartz powder | 100 |
| | Sodium p-toluene-sulfinate | 0.2 |
| | N,N'—diethanol-p-toluidine | 0.4 |

TABLE 12

| Example No. | Acrylate Compound | Amount (parts by weight) of Acrylate Compound | Adhesion Strength (kg/cm²) to Enamel of Bovine Tooth | Adhesion Strength (kg/cm²) to Ni—Cr |
|---|---|---|---|---|
| 45 | A | 5 | 135 | 315 |
| 46 | A | 10 | 150 | 320 |
| 47 | A | 20 | 165 | 315 |
| 48 | A | 40 | 150 | 302 |
| 49 | B | 10 | 128 | 275 |
| 50 | C | 10 | 142 | 290 |
| 51 | D | 10 | 130 | 284 |
| 52 | D | 20 | 135 | 293 |
| 53 | E | 10 | 124 | 276 |
| 54 | F | 10 | 122 | 269 |
| Comparative Example | | | | |
| 10 | not added | — | 70 | 95 |
| 11 | R | 10 | 95 | 163 |
| 12 | S | 10 | 98 | 187 |

EXAMPLES 55 THROUGH 60 AND COMPARATIVE EXAMPLE 13

The adhesion strength of the adhesive composition of the present invention to a Co—Cr alloy was measured. A test piece was prepared in the same manner as described in Examples 7 through 12, and an adhesive composition shown in Table 13 was cured at 23° C., the test piece was immersed in water at 37° C. for 24 hours, and the tensile strength was measured. Incidentally, just before bonding, 1 part by weight of a liquid was mixed with 1.6 parts of a powder for about 20 seconds. The obtained results are shown in Table 14.

TABLE 13

| | Component | Amount (parts by weight) |
|---|---|---|
| Liquid | MMA | 80 |
| | Acrylate compound | 20 |
| | BPO | 1 |
| | BHT | 0.05 |
| Powder | PMMA | 90 |
| | PEMA | 10 |
| | Sodium p-toluene-sulfinate | 0.3 |
| | N,N'—diethanol-p-toluidine | 0.5 |

TABLE 14

| | Acrylate Compound | Adhesion Strength (kg/cm$^2$) to Co—Cr |
|---|---|---|
| Example No. | | |
| 55 | A | 305 |
| 56 | B | 285 |
| 57 | C | 286 |
| 58 | D | 295 |
| 59 | E | 275 |
| 60 | F | 270 |
| Comparative Example | | |
| 13 | not added | 84 |

EXAMPLES 61 THROUGH 69 AND COMPARATIVE EXAMPLES 14 THROUGH 16

In the same manner as described in Examples 29 through 39, an imitation cavity was formed in the dentine of a bovine tooth, and an adhesive composition shown in Table 15 was coated and a photo-curable composite resin shown in Table 16 was filled in the cavity. The tooth was irradiated with rays emitted from a commercially available visible ray irradiator ("Optilux" supplied by Demetron) for 30 seconds to cure the composite resin. The paraffin wax was removed and the tooth was stored in water at 37° C. for 24 hours. A metal attachment was attached to the test piece and the tensile adhesion strength was measured by using a tensile tester at a crosshead speed of 10 m/min. The obtained results are shown in Table 17.

TABLE 15

| Component | Amount (parts by weight) |
|---|---|
| Bis-GMA | 27 |
| 3G | 43 |
| HEMA | 20 |
| Acrylate compound | shown in Table 17 |
| Camphorquinone | 0.4 |
| N,N—Dimethyl-p-toluidine | 0.4 |
| HQME | 0.05 |

TABLE 16

| Component | Amount (parts by weight) |
|---|---|
| Bis-GMA | 42 |
| 3G | 28 |
| Tetramethylolmethane triacrylate | 30 |
| Camphorquinone | 0.4 |
| N,N—Dimethyl-p-toluidine | 0.4 |
| HQME | 0.05 |
| Silane-treated fine quartz powder | 200 |

TABLE 17

| Example No. | Acrylate Compound | Amount (parts by weight) of Acrylate Compound | Adhesion Strength (kg/cm$^2$) |
|---|---|---|---|
| 61 | A | 10 | 35 |
| 62 | A | 20 | 42 |
| 63 | A | 40 | 36 |
| 64 | B | 10 | 29 |
| 65 | C | 10 | 30 |
| 66 | D | 10 | 32 |
| 67 | D | 20 | 35 |
| 68 | E | 10 | 26 |
| 69 | F | 10 | 29 |
| Comparative Example | | | |
| 14 | not added | — | 0 (peeling on removal of paraffin wax) |
| 15 | R | 10 | 0 (peeling by immersion in water at 37° C.) |
| 16 | S | 10 | 0 (peeling by immersion in water at 37° C.) |

EXAMPLES 70 THROUGH 73

Adhesive compositions were prepared in the same manner as described in Examples 61 through 69 except that 20 parts by weight of the acrylate compound A was used and the photo-sensitizer and curing promotor were changed as shown in Table 18, and the adhesion strength was measured by the method described in Examples 61 through 69. The obtained results are shown in Table 18.

TABLE 18

| Example No. | Photo-sensitizer (parts by weight) | Curing Promotor (parts by weight) | Adhesion Strength (kg/cm$^2$) |
|---|---|---|---|
| 70 | camphorquinone (0.5) | N,N'—dimethylbenzyl amine (0.5) | 40 |
| 71 | benzyl (1.0) | N,N'—dimethyl-p-toluidine (0.5) | 32 |
| 72 | 2,4-diethoxythio-xanthone (0.8) | N,N'—dimethyl-p-toluidine (0.4) | 30 |
| 73 | α-naphtyl (1.0) | diemthylaminoethyl methacrylate (1.0) | 28 |

EXAMPLES 74 THROUGH 79

In the same manner as described in Examples 45 through 54, the enamel of a bovine tooth and an Ni—Cr alloy were treated, and a double-coated tape having a thickness of 0.1 mm and a hole diameter of 5 mm was applied, and an adhesive composition shown in Table 19 was coated in the hole and a polypropylene film having a thickness of 6 μm was placed thereon. Then, the test piece was irradiated with ultraviolet rays for 1 minute by a commercially available ultraviolet irradiator (Nuvalight supplied by L. D. Caulk) to effect curing. The polypropylene film was removed and a metal attachment was attached to the test piece, and the tensile adhesion strength was measured by a tensile tester. The obtained results are shown in Table 20.

TABLE 19

| Component | Amount (parts by weight) |
|---|---|
| Bis GMA | 30 |
| 3G | 40 |

TABLE 19-continued

| Component | Amount (parts by weight) |
|---|---|
| NPG | 20 |
| Acrylate compound (A) | 10 |
| Photo-sensitizer | shown in Table 20 |
| Curing promotor | shown in Table 20 |

TABLE 20

| Example No. | Photo-sensitizer (parts by weight) | Curing Promotor (parts by weight) | Adhesion Strength ($kg/cm^2$) to Enamel of Bovine Tooth | Adhesion Strength ($kg/cm^2$) to Ni—Cr |
|---|---|---|---|---|
| 74 | benzoin methyl ether (1.0) | — | 128 | 265 |
| 75 | benzoin methyl ether (1.0) | dioctyl phosphite (0.5) | 142 | 285 |
| 76 | benzoin isopropyl ether (1.0) | — | 135 | 273 |
| 77 | benzoin isopropyl ether (1.5) | 2-thiobarbituic acid (0.3) | 145 | 295 |
| 78 | benzophenone (1.0) | N,N'—dimethyl-p-toluidine (0.5) | 140 | 284 |
| 79 | P,P'—dimethylamino-benzophenone (1.0) | — | 130 | 271 |

We claim:

1. An acrylate compound represented by the following general formula:

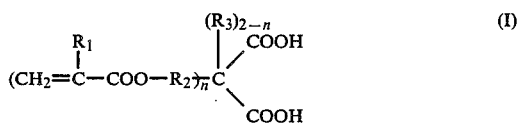
(I)

wherein $R_1$ stands for a hydrogen atom or an alkyl group having 1 to 4 carbon atoms, $R_2$ stands for an alkylene group having 2 to 20 carbon atoms, $R_3$ stands for a hydrogen atom or an alkyl group having 1 to 20 carbon atoms when n is 1, and n is 1 or 2.

2. An acrylate compound as set forth in claim 1, wherein in the general formula (I), $R_1$ stands for a hydrogen atom or a methyl group, $R_2$ stands for an alkylene group having 4 to 12 carbon atoms, $R_3$ stands for a hydrogen atom or an alkyl group having 1 to 4 carbon atoms, and n is 1.

3. An ω-methacryloxy-α,α-alkanedicarboxylic acid.

4. An ω-acryloxy-α,α-alkanedicarboxylic acid.

5. 11-Methacryloxy-1,1-undecanedicarboxylic acid.

6. An acrylate compound as set forth in claim 1, wherein in the general formula (I), $R_2$ stands for an alkylene group having 4 to 12 carbon atoms.

7. An acrylate compound as set forth in claim 1, wherein in the general formula (I), $R_1$ stands for hydrogen, methyl or ethyl.

8. An acrylate compound as set forth in claim 1, wherein in the general formula (I), n is 1.

9. An acrylate compound as set forth in claim 8, wherein in the general formula (I), $R_3$ stands for a hydrogen atom or an alkyl group having 1 to 4 carbon atoms.

* * * * *